(12) United States Patent
Eeckman et al.

(10) Patent No.: US 8,563,036 B2
(45) Date of Patent: Oct. 22, 2013

(54) PHARMACEUTICAL COMPOSITIONS COMPRISING BRIVARACETAM

(75) Inventors: Frédéric Eeckman, Brussels (BE); Domenico Fanara, Brussels (BE); Monique Berwaer, Brussels (BE)

(73) Assignee: UCB Pharma, S.A., Brussels (BE)

( * ) Notice: Subject to any disclaimer, the term of this patent is extended or adjusted under 35 U.S.C. 154(b) by 7 days.

(21) Appl. No.: 13/148,175

(22) PCT Filed: Feb. 5, 2010

(86) PCT No.: PCT/EP2010/051422
§ 371 (c)(1),
(2), (4) Date: Oct. 5, 2011

(87) PCT Pub. No.: WO2010/089372
PCT Pub. Date: Aug. 12, 2010

(65) Prior Publication Data
US 2012/0040006 A1 Feb. 16, 2012

(30) Foreign Application Priority Data
Feb. 9, 2009 (EP) .................................. 09100104

(51) Int. Cl.
*A61K 9/22* (2006.01)
*A61K 9/20* (2006.01)

(52) U.S. Cl.
CPC ................................ *A61K 9/2077* (2013.01)
USPC ......................................... 424/468; 424/490

(58) Field of Classification Search
None
See application file for complete search history.

(56) References Cited

U.S. PATENT DOCUMENTS

2009/0263481 A1* 10/2009 Patil et al. ..................... 424/472

FOREIGN PATENT DOCUMENTS

| EP | 1 731 149 A1 | 12/2006 |
| WO | WO 2007141002 A1 * | 12/2007 |
| WO | 2008/006528 A2 | 1/2008 |
| WO | WO 2010/026467 | 3/2010 |

OTHER PUBLICATIONS

"Lactose" from Wikipedia retrieved online on Mar. 20, 2013 (p. 1-3) (http://en.wikipedia.org/wiki/Lactose).*
Malawska, B. et al., "Brivaracetam: a new drug in development for epilepsy and neuropathic pain", Expert Opinion on Investigational Drugs, Mar. 2008, 362.
Kasteleijn-Nolst Trenite, D.G.A. et al., "New analogue of levetiracetam Brivaracetam and its efficacy in the photosensitivity model", Aug. 2005, Epilepsia, Conference 26th International Epilepsy Congress, 46.

* cited by examiner

*Primary Examiner* — Bethany Barham
(74) *Attorney, Agent, or Firm* — McDonnell Boehnen Hulbert & Berghoff LLP

(57) ABSTRACT

The present invention relates to a pharmaceutical composition comprising brivaracetam as active ingredient, the invention relates specifically to a prolonged release formulation.

7 Claims, No Drawings

PHARMACEUTICAL COMPOSITIONS COMPRISING BRIVARACETAM

This application is a US national phase of International Application No. PCT/EP2010/051422 filed on Feb. 5, 2010, the disclosure of which is incorporated herein by reference in its entirety.

The present invention relates to a novel pharmaceutical composition comprising Brivaracetam.

International patent application having publication number WO 01/62726 discloses 2-oxo-1-pyrrolidine derivatives and methods for their preparation. It particularly discloses compound (2S)-2-[(4R)-2-oxo-4-propyl-pyrrolidin-1-yl]butanamide known under the international non propriety name of Brivaracetam.

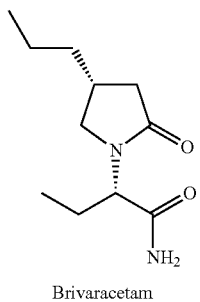

Brivaracetam

Brivaracetam is effective in the treatment of epilepsy. Clinical trials evaluated the efficacy and safety of Brivaracetam (2.5, 5, 20 and 50 mg per day) in the adjunctive treatment of adult patients (16-65 years) with refractory partial onset seizures, with or without secondary generalization. Brivaracetam is also effective in the treatment of patients (>18 years) with post-herpetic neuralgia.

One of the objectives currently sought in the development of pharmaceutical compositions which can be administered orally is to control the release of pharmaceutically active substances so that they can be administered in a few daily doses, ideally in a single daily dose.

It is indeed of great advantage to both the patient and the physician that medication can be formulated so that it may be administered in a minimum number of daily doses from which the drug is uniformly released over a desired extended period of time. This effect is accomplished using sustained release compositions. Sustained release compositions containing pharmaceutical medicaments or other active ingredients are designed to contain higher concentrations of the medicament and are prepared in such a manner as to obtain an effect sustained release into the gastrointestinal digestive tract of humans over an extended period of time.

Well absorbed oral sustained release therapeutic drug dosage forms have inherent advantages over conventional, immediate release dosage forms. The advantages include less frequent dosing of a medicament and resultant patient regime compliance, a more sustained drug blood level response, therapeutic action with less ingested drug and the mitigation of side effects. By providing a slow and steady release of the medicament over time, absorbed drug concentration spikes are mitigated or eliminated by showing a smoother and more sustained blood level response.

For this purpose, a controlled release formulation has to meet some criteria; namely, it must induce an uniform and constant dissolution of the drugs, and it must be effective for an extended period of time. It is also important that such a formulation be simple to make, that the manufacturing process be reproducible and that the product produced by the manufacturing process be uniform.

Brivaracetam is a freely water soluble active ingredient (ca. 700 mg/ml), and it is not obvious to slow down the release of the drug.

Moreover another problem consists in the reduction of the release rate, while keeping a reasonable size to the pharmaceutical form given to the patients.

One of the objectives of the invention is a pharmaceutical composition which can be administered orally to control the release of pharmaceutically active substances so that it can be administered in a few daily doses, ideally in a single daily dose and so to provide a therapeutic effect for at least 16 hours when administered to a patient.

Considering Brivaracetam is classified as BCS I, the resulting in vitro dissolution (USP <711> apparatus No 2) in a buffered aqueous media has to show a drug release of no more than 40% after 1 hour of dissolution, of 35%-80% after 4 hours of dissolution and of no less than 80% after 16 hours of dissolution. Preferably, a profile of no more than 35% after 1 hour of dissolution, of 40%-75% after 4 hours of dissolution and of no less than 80% after 16 hours of dissolution. More preferably a profile of no more than 30% after 1 hour of dissolution, of 45%-70% after 4 hours of dissolution and of no less than 80% after 16 hours of dissolution.

The present invention relates to a pharmaceutical composition in the form of a solid oral dosage form having Brivaracetam as active ingredient and, as excipient within the core of the pharmaceutical form, 5% to 90% per weight of at least one matrix agent chosen among hydrophobic matrix agents and inert matrix agents, with respect to the total weight of the core of the pharmaceutical form.

By the term "solid oral dosage form" as used herein, we understood tablets, granules or capsules. Tablets can be obtained by either direct compression, wet granulation, extrusion-spheronisation, or any technique known by those skilled in the art. Granules can be obtained by granulation, melt extrusion, or any technique known by those skilled in the art. Usually capsules contain waxy formulations or granulates.

The term "active ingredient" as used herein is defined as a substance which has a therapeutic effect.

The amount of the active ingredient present in the pharmaceutical composition of the invention may vary depending on the patient to which the compositions are administered and on the disease to be treated.

The term "core of the pharmaceutical form" as used herein is defined as the pharmaceutical composition without coating. All the percentages are given per weight of the total weight of the core of the pharmaceutical form, except when it is written otherwise.

The term "matrix agent" as used herein is defined as a pharmaceutical acceptable excipient that can retard the release of an active pharmaceutical ingredient. The matrix agent of the invention can be a polymer (also called inert agent) or a non-polymer material (also called hydrophobic agent). The non-polymer material of the matrix agent is selected among long chain alcohols and lipids, like waxes, fatty acids or fats.

Usually the non-polymer hydrophobic material used in the present invention has a melting point greater than about 40° C. The hydrophobic material used in the present invention has a melting point generally from about 43° C. to about 100° C.; preferably from about 0.43° C. to about 90° C., more preferably from about 50° C. to about 80° C. It is important to note that the presence of lubricants and/or other hydrophobic material may affect the melting range. However, the melting range of the hydrophobic material when associated with these other material in the formulation should not fall below body temperature.

Usually the hydrophobic matrix agents of the invention are chosen among fatty acids which are carboxylic acids derived from or contained in an animal or vegetable fat or oil. Fatty acids are composed of a chain of alkyl groups containing from 4 to 22 carbon atoms and are characterized by a terminal carboxyl group. Fatty acids useful in the present invention are selected from the group consisting of hydrogenated palm oil, hydrogenated palm kernel oil, hydrogenated peanut oil, hydrogenated rapeseed oil, hydrogenated rice bran oil, hydrogenated soybean oil, hydrogenated cottonseed oil, hydrogenated sunflower oil, hydrogenated castor oil, and the like, or mixtures thereof. Other fatty acids include, for example, decenoic acid, docosanoic acid, stearic acid, palmitic acid, lauric acid, myristic acid, and the like, and mixtures thereof. The preferred fatty acids are selected from the group consisting of hydrogenated palm oil, hydrogenated castor oil, hydrogenated cottonseed oil, stearic acid, palmitic acid, and mixtures thereof.

In another embodiment, the matrix agents of the invention are chosen among long chain alcohols, i.e. C8-C30 alcohols. Generally, long chain monohydric alcohols, preferably C8-C22 alcohols, such as cetyl alcohol, stearyl alcohol and mixtures thereof are used.

In another embodiment, the matrix agents of the invention are chosen among waxes. Waxes are esters of fatty acids with long chain (C8-C22) monohydric alcohols. Natural waxes are often mixtures of such esters, and may also contain hydrocarbons. Waxes are low-melting organic mixtures or compounds having a high molecular weight and are solid at room temperature. Waxes may be hydrocarbons or esters of fatty acids and alcohols. Waxes useful in the present invention include natural waxes, such as animal waxes vegetable waxes, and petroleum waxes (i.e., paraffin waxes, microcrystalline waxes, petrolatum waxes, mineral waxes), and synthetic waxes which are edible and have a melting point within the range from about 25° C. to about 100° C. Specific examples useful waxes are spermaceti wax, carnauba wax, Japan wax, bayberry wax, flax wax, beeswax, Chinese wax, shellac wax, lanolin wax, sugarcane wax, candelilla wax, paraffin wax, microcrystalline wax, petrolatum wax, and the like, and mixtures thereof. Mixtures of these waxes with the fatty acids set out above may also be used.

The wax may also be a monoglyceryl ester, diglyceryl ester, or triglyceryl ester (glycerides) which is an ester formed from a fatty acid having from about 10 to about 22 carbon atoms and glycerol, wherein one or more of the hydroxyl groups of glycerol are substituted by a fatty acid. Examples of useful glycerides include glyceryl monostearate, glyceryl distearate, glyceryl tristearate, glyceryl dipalmitate, glyceryl tripalmitate, glyceryl monopalmitate, glyceryl dilaurate, glyceryl trilaurate, glyceryl monolaurate, glyceryl didocosanoate, glyceryl tridocosanoate, glyceryl monodocosanoate, glyceryl monocaproate, glyceryl dicaproate, glyceryl tricaproate, glyceryl monomyristate, glyceryl dimyristate, glyceryl trimyristate, glyceryl monodecenoate, glyceryl didecenoate, glyceryl tridecenoate, glyceryl behenate, Macrogolglycerides and the like, and mixtures thereof.

The preferred waxes may be selected from Hydrogenated castor oil, Glyceryl behenate (Compritol®), Hydrogenated soybean oil, Lauroyl macrogolglycerides (Gelucire 44/14®), Stearyl macrogolglycerides (Gelucire 50/13®), Glyceryl Palmitostearate (Precirol®), glycerol esters of fatty acids (Gelucire 43/01® and Gelucire 39/01®), Cetyl alcohol, and mixtures thereof.

The amount of non polymeric matrix agent used in the formulation may vary depending upon the size of the pharmaceutical form and the degree of sustained release desired. In general, the fatty acid or waxy edible material will be present in the core in an amount from about 5% to about 90%, preferably from about 10% to about 75%, and more preferably from about 15% to about 60%, by weight of the composition.

In another embodiment of the invention, the matrix agents of the invention are chosen among inert polymers. Polymers according to the invention are the excipients whose performance is usually independent of the pH of the environment. They do not swell/dissolve in water and can therefore act as controlled release agent. Such materials are frequently referred to as inert matrixes.

Such polymers comprise, but are not limited to polymethacrylic acid derivatives, such as ethyl acrylate methyl methacrylate copolymer (Eudragit NE®); cellulose derivatives such as ethyl cellulose and cellulose acetate; or non-water soluble polyesters, such as polylactic acid. Preferably, the polymers are chosen among polymethacrylic acid derivatives.

Usually, the amount of pH independent polymer used in the formulation may vary depending upon the dose and the degree of sustained release desired. In general, these polymers will be present in the formulation in an amount from about 5% to about 90%, preferably from about 15% to about 75%, and more preferably from about 20% to about 60%, by weight of the composition.

The inert matrix agent may consist of one component or be a mixture of two or more components, as defined herein.

The composition of the invention therefore typically includes pharmaceutically acceptable excipients. As is well known to those skilled in the art, pharmaceutical excipients are routinely incorporated into solid dosage forms. This is done to ease the manufacturing process as well as to improve the performance of the dosage form. Common excipients include diluents, lubricants, granulating aids, colorants, flavorants, surfactants, pH adjusters; anti-adherents and gildants etc. Such excipients are routinely used in the dosage forms of this invention.

The term "gliding agent" as used herein is defined as an agent improving the fluidity of the powder and thus the filling of the granulation machine and the tablet press. The gliding agent may be present in the pharmaceutical composition in the form of a single compound or in the form of a mixture of compounds.

Examples of gliding agents are, but not limited to, talc, starches, stearic acid and anhydrous colloidal silica.

Usually, the pharmaceutical composition according to the present invention comprises 0.0 to 3.0% per weight of gliding agent. Preferably, the pharmaceutical composition according to the present invention comprises 0.0 to 1.5% per weight of gliding agent. More preferably, the pharmaceutical composition according to the present invention comprises 0.0 to 1.0% per weight of gliding agent The pharmaceutical composition of the invention may also comprise a lubricant, as excipient within the core of the pharmaceutical form The term "lubricant" as used herein is defined as an agent able to decrease adhesion of a powder to punches and friction between particles. The lubricant may be present in the pharmaceutical composition in the form of a single compound or in the form of a mixture of compounds.

Examples of lubricants are, but not limited to, talc, magnesium stearate, calcium stearate, poloxamer, sodium lauryl sulfate, stearic acid, Sodium Stearyl Fumarate or macrogol (also referred to as polyethylene glycol or PEG).

Usually, the pharmaceutical composition according to the present invention comprises 0.0 to 5.50% per weight of lubricant with respect to the total weight of the core of the pharmaceutical form.

Preferably, the pharmaceutical composition according to the present invention comprises 0.0 to 4.50% per weight of lubricant with respect to the total weight of the core of the pharmaceutical form.

More preferably, the pharmaceutical composition according to the present invention comprises 0.0 to 3.50% per weight of lubricant with respect to the total weight of the core of pharmaceutical form.

The pharmaceutical composition of the invention may also comprise diluents as excipient within the core of the pharmaceutical form.

The term "diluent" as used herein is defined as an agent used as filler in order to achieve the desired pharmaceutical form volume or weight. The diluent may be present in the pharmaceutical composition in the form of a single compound or in the form of a mixture of compounds.

Examples of diluent are, but not limited to, lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

Usually, the pharmaceutical composition according to the present invention comprises 0.0 to 75% per weight of diluent with respect to the total weight of the core of the pharmaceutical form.

Preferably, the pharmaceutical composition according to the present invention comprises 0 to 60% per weight of diluent with respect to the total weight of the core of the pharmaceutical form.

More preferably, the pharmaceutical composition according to the present invention comprises 0 to 40% per weight of diluent with respect to the total weight of the core of the pharmaceutical form.

The pharmaceutical composition of the invention may also comprise binders as excipient within the core of pharmaceutical form.

The term "binder" as used herein is defined as an agent used to increase the cohesion of the granules during the compression, in order to obtain pharmaceutical forms with a defined hardness, or to act as processing aid during the wet granulation process. The binder may be present in the pharmaceutical composition in the form of a single compound or in the form of a mixture of compounds.

Examples of binders are, but not limited to, starch, microcrystalline cellulose, silicified microcrystalline cellulose, carboxymethylcellulose, Hydroxypropyl methylcellulose, dextrin, maltodextrin, povidone (PVP), methylcellulose, pregelatinized starch.

Preferred binders are microcrystalline cellulose for direct compression or dry granulation tablets, and pregelatinized starch and povidone for wet granulation tablets.

Usually, the pharmaceutical composition according to the present invention comprises 0.0 to 80% per weight of binder with respect to the total weight of the core of the pharmaceutical form.

Preferably, the pharmaceutical composition according to the present invention comprises 1 to 70% per weight of binder with respect to the total weight of the core of the pharmaceutical form.

More preferably, the pharmaceutical composition according to the present invention comprises 2 to 60% per weight of binder with respect to the total weight of the core of the pharmaceutical form.

Optionally, the pharmaceutical form which is in a tablet or a granule form may be coated by either an active coating or a cosmetic/taste masking coating.

By "active" coating, it is understood a coating bringing about a significant change in the dissolution properties of the pharmaceutical form, like an enteric effect, a delaying effect or an additional sustained release effect.

The pharmaceutical composition of the invention can be manufactured by any process according to conventional methods known to the man skilled in the art.

Examples of processes are direct compression, dry granulation, wet granulation, melt granulation, pellitization or liquid filling.

For wet granulation processes, the active ingredient could either be placed within the internal phase as a solid material, in the external phase as a solid material, be dissolved in the liquid phase or a mix of thereof. The matrix agents could either be incorporated in the liquid phase, in the internal phase, as solid materials, or in the external phase, or a mix of thereof.

The process may comprise a further coating step in which water, preferably purified water, is added to the coating agent and resulting suspension/solution is sprayed on the core of the pharmaceutical form.

In another aspect the present invention relates to a pharmaceutical composition comprising Brivaracetam useful for the treatment or prevention of a disease.

By the term "disease", we understand a disease selected from the group consisting of epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless leg syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

The term "treatment" as used herein, includes curative treatment and prophylactic treatment.

By "curative" is meant efficacy in treating a current symptomatic episode of a disorder or condition.

By "prophylactic" is meant prevention of the occurrence or recurrence of a disorder or condition.

The present invention concerns also a method for treatment of a human patient by using the pharmaceutical composition.

The present invention concerns also the pharmaceutical composition for use as a medicament for curing the said disease.

The present invention concerns also the use of the pharmaceutical composition for the manufacture of a medicament for a therapeutic application in the said disease.

Preferably said disease is selected from the group consisting essentially of epilepsy, Parkinson's disease, dyskinesia, migraine, tremor, essential tremor, bipolar disorders, chronic pain, neuropathic pain, or bronchial, asthmatic or allergic conditions. More preferably said disease is epilepsy.

The present invention concerns also a method for manufacturing a medicament intended for therapeutic application in the said disease, characterized in that the pharmaceutical composition according to the present invention is used.

The present invention is also directed to methods of treating humans to alleviate disease by the administration of the pharmaceutical composition.

The following examples are provided for illustrative purposes only and are not intended, nor should they be construed, as limiting the invention in any manner. Those skilled in the art will appreciate that routine variations and modifications of the following examples can be made without exceeding the spirit or scope of the invention.

EXAMPLES

Example 1

Sustained release hard gelatine capsules containing 50 mg of Brivaracetam and waxy solid sold under the trademark Gelucire 50/13 are prepared by liquid filling. The filling process was performed at a temperature above 50° C.

TABLE 1

| Composition of Gelucire 50/13 capsules | | |
| --- | --- | --- |
| Component | mg | % |
| Brivaracetam | 50 | 20 |
| Gelucire 50/13 | 200 | 80 |

Gelucire 50/13 is composed of stearoyl macroglycerides (PEG-32 glyceryl palmitostearate). Its HLB value is 13 and its melting temperature is about 50° C.

TABLE 2

| results in % | | | |
| --- | --- | --- | --- |
| Time (Hours) | 1.00 | 4.00 | 16.00 |
| % released | 37 | 76 | 100 |

The in vitro dissolution profiles in water were determined according to the USP <711> (apparatus n° 2, 50 rpm, aqueous medium 900 mL) over an interval of time of 16 h. The dissolution was conducted at 37° C. in a pH 6.4 phosphate buffer.

Capsules show a sustained release of the Brivaracetam what comply with the in vitro dissolution requirements Example 2

Sustained release hard gelatine capsules containing 50 mg of Brivaracetam and waxy solid agent sold under the trademark Gelucire 43/01 are prepared by liquid filling.

TABLE 3

| Composition of Gelucire 43/01 capsules | | |
| --- | --- | --- |
| Component | mg | % |
| Brivaracetam | 50 | 40 |
| Gelucire 43/01 | 75 | 60 |

Gelucire 43/01 is a glycerol ester of fatty acids glycerol esters of saturated C12-C18 fatty acids). Its HLB value is 1 and its melting temperature is about 43° C.

TABLE 4

| results in % | | | |
| --- | --- | --- | --- |
| Time (Hours) | 1.00 | 4.00 | 16.00 |
| % released | 26 | 45 | 80 |

The in vitro dissolution profiles in water were determined according to the USP <711> (apparatus n° 2, 50 rpm, aqueous medium 900 mL) over an interval of time of 16 h. The dissolution was conducted at 37° C. in a pH 6.4 phosphate buffer.

Capsules show a sustained release of the Brivaracetam what comply with the in vitro dissolution requirements Example 3

Sustained release hard gelatine capsules containing 50 mg of Brivaracetam and Precirol ATO 05 are prepared by liquid filling.

TABLE 5

| Composition of the capsules | | |
| --- | --- | --- |
| Component | Mg | % |
| Brivaracetam | 50 | 60 |
| Precirol ATO 05 | 33.3 | 40 |

Precirol ATO 5 is the trade name for a glyceryl palmitostearate. Its melt temperature is about 56° C. and its HLB value is 2.

TABLE 6

| results in % | | | |
| --- | --- | --- | --- |
| Time (Hours) | 1.00 | 4.00 | 16.00 |
| % released | 38 | 50 | >95 |

The in vitro dissolution profiles in water were determined according to the USP <711> (apparatus n° 2, 50 rpm, aqueous medium 900 mL) over an interval of time of 16 h. The dissolution was conducted at 37° C. in a pH 6.4 phosphate buffer.

Capsules show a sustained release of the Brivaracetam what comply with the in vitro dissolution requirements.

Example 4

Sustained release size tablets containing 50 mg of Brivaracetam and Precirol ATO 05 are prepared by direct compression.

TABLE 7

| Composition of the tablets | |
| --- | --- |
| Product | Proportions mg |
| Brivaracetam | 50 |
| Precirol ATO 5 | 247 |
| Microcrystalline cellulose | 36.8 |
| Lactose monohydrate | 73.7 |
| Magnesium stearate | 3.0 |
| Anhydrous colloidal silica | 1.5 |

Precirol ATO 05 is composed of glycerylpalmitostearate. Microcrystalline cellulose is sold under the trademark Avicel PH102. It is used as binder. Lactose monohydrate is used as a filler. Anhydrous colloidal silica is used as gliding agent.

TABLE 8

| | results in % | | |
|---|---|---|---|
| Time (Hours) | 1.00 | 4.00 | 16.00 |
| % released | 21 | 78 | 100 |

The in vitro dissolution profiles in water were determined according to the USP <711> (apparatus n° 2, 50 rpm, aqueous medium 900 mL) over an interval of time of 16 h. The dissolution was conducted at 37° C. in a pH 6.4 phosphate buffer.

Tablets show a sustained release of the Brivaracetam that comply with the in vitro dissolution requirements.

Example 5

All experiments were performed in accordance with the Guidelines of the local Ethical Committee for Animal Experimentation.

Epileptiform responses in hippocampal slices: Levetiracetam reduces epileptiform responses induced in rat hippocampal slices by high-K+/low-Ca2+ concentrations in the perfusion fluid and induced by bicuculline. The effect of brivaracetam on epileptiform responses induced by high-K+/low-Ca2+ concentrations or by bicuculline was examined in transverse hippocampal slices prepared from Sprague-Dawley rats according to previously reported standard procedures. The epileptiform responses were induced by passing from a normal perfusion of artificial cerebrospinal fluid (ACSF) (K+3 mM; Ca2+2.4 mM) to either high-K+/low-Ca2+ fluid (HKLCF) (K+7.5 mM; Ca2+0.5 mM) or to 5 M bicuculline methiodide (BMI)-containing ACSF.

Extracellular field potentials (FPs) were recorded in the CA3 area of the slices with 2 M NaCl-filled glass microelectrodes. The evoked FPs were recorded at 10-min intervals in response to fimbrial stimulation with constant current rectangular pulses that elicit a single population spike (PS) of 50-75% of the maximal amplitude when the slice is in ACSF. In the HKLCF model, 2 min of spontaneous activity were also recorded, in the middle of each 10-min interval between the recordings of evoked responses.

Either brivaracetam or levetiracetam was added to the bathing fluid of the slices 20 min before shifting from ACSF to either HKLCF or 5 M BMI-containing ACSF, and was kept in the perfusion fluid throughout the experiment.

Audiogenic seizures in mice: Genetically sound-sensitive male mice (16-28 g; n=10 per group), responding with wild running, clonic and tonic convulsions to an acoustic stimulation, were used. Audiogenic seizures were induced by an acoustic stimulus (90 dB, 10-20 kHz) applied for 30 s. The mice were pretreated with either saline, brivaracetam (i.p., 30 min) or levetiracetam (i.p., 60 min), and the proportion of mice protected against clonic convulsions was used as the end point to assess anticonvulsant activity.

Chemically induced seizures in mice: Pentylenetetrazol, 83 mg kg-1 s.c., was used to evaluate the anticonvulsant properties of brivaracetam. The dose was selected based on dose-effect curves in saline-treated animals as the convulsive dose inducing clonic convulsions of all four extremities in 97% of the animals. Immediately after administration of the chemoconvulsant, the mice were placed individually in small plastic cages (25 13 8 cm) and observed for the presence of clonic convulsions in all four extremities, for 60 min. The occurrence of tonic convulsions (hindlimb extension) and mortality was also recorded during this interval. The proportion of mice protected against clonic convulsions was calculated and used as the end point for anticonvulsant activity.

Results

Epileptiform responses in hippocampal slices: Changing the perfusion of rat hippocampal slices from the normal ACSF to HKLCF produced increasingly epileptiform FPs in the CA3 area in response to constant-current fimbrial stimulation. In control slices exposed to HKLCF alone, the PS1 amplitude progressively increased, reaching plateau values within 20 min (4.250.77 mV), nearly twofold higher than those recorded under ACSF perfusion (2.180.15 mV; means. d. for n=10 slices). Also, constant-current single stimuli-evoked bursts of repetitive PSs (that is, PS2, PS3 and so on) increased markedly in number in the first 30 min of HKLCF perfusion from the single PS1 to an average of 7.62.3 PS per evoked burst, and continued to increase slightly up to the end of the records, reaching an average of 8.81.6 PS per evoked burst after 80-min perfusion of HKLCF. Both brivaracetam and levetiracetam reduced these epileptiform responses. Upon 15-min perfusion of HKLCF, spontaneous field bursts occurred in 4 out of the 10 control slices exposed to HKLCF alone, whereas from 25 min in HKLCF to the end of the records, all control slices presented regular field bursting. Brivaracetam (3.2 M), but not levetiracetam (32 M), reduced the rate of this spontaneous bursting.

In vivo studies: In fully amygdala-kindled rats, brivaracetam induced a significant suppression in motor-seizure severity from a dose of 21.2 mg kg-1, whereas levetiracetam induced a similar effect from a dose of 170 mg kg-1. Brivaracetam also significantly reduced the after-discharge duration at the highest dose tested (212.3 mg kg-1), whereas levetiracetam was inactive on this parameter up to 1700 mg kg-1.

Audiogenic seizure-susceptible mice were protected against the expression of clonic convulsions by brivaracetam and levetiracetam. Brivaracetam, administered i.p. 30 min before seizure induction in mice, also protected against clonic convulsions induced by pentylenetetrazol and against tonic hindlimb extension induced by a maximal electroshock in mice, although with higher ED50 values.

Brivaracetam significantly suppressed spontaneous SWDs in GAERS rats from a dose of 2.1 mg kg-1 with complete inhibition appearing at the highest dose tested (67.9 mg kg-1).

Pretreatment with brivaracetam during corneal kindling of mice resulted in a significant reduction in the incidence of generalized motor seizures, and a similar incidence reduction was observed with levetiracetam at higher doses. Continued corneal stimulations following termination of treatment showed a persistent reduction in the incidence of generalized motor seizures in the group previously treated with the highest dose of brivaracetam.

The invention claimed is:

1. A sustained release pharmaceutical composition comprising a core and, optionally, a coating, wherein the core comprises Brivaracetam as active ingredient and, as an excipient, at least one hydrophobic matrix agent or inert matrix agent in an amount that is 5% to 90% by weight of the composition, the matrix agent being a polymer which is a polymethacrylic acid derivative, or a non-polymer material which is a C8-C30 alcohol or lipid, or a non-polymer material having a melting point greater than 40° C., and wherein the composition is in solid form, and wherein the amount of Brivaracetam released in an in vitro buffered aqueous media (USP <711>Apparatus 2) is no more than 40% after 1 hour, 35%-80% after 4 hours, and no less than 80% after 16 hours.

2. The pharmaceutical composition according to claim 1, wherein the non-polymer material has a melting point from 43° C. to 80° C.

3. The pharmaceutical composition according to claim 1 or 2, wherein the matrix agent is a fatty acid from or contained in an animal or vegetable fat or oil.

4. The pharmaceutical composition according to claim 3, wherein the fatty acid is hydrogenated palm oil, hydrogenated castor oil, hydrogenated cottonseed oil, stearic acid, palmitic acid, or a mixture thereof.

5. The pharmaceutical composition according to claim 1, wherein the matrix agent is a C8-C30 monohydric alcohol.

6. The pharmaceutical composition according to claim 1 wherein the matrix agent is a wax.

7. The pharmaceutical composition according to claim 6, wherein the wax is hydrogenated castor oil, glyceryl behenate, hydrogenated soybean oil, lauroyl macrogolglycerides, stearyl macrogolglycerides, glyceryl palmitostearate, glycerol esters of fatty acids, cetyl alcohol, or a mixture thereof.

\* \* \* \* \*

UNITED STATES PATENT AND TRADEMARK OFFICE
CERTIFICATE OF CORRECTION

| | | |
|---|---|---|
| PATENT NO. | : 8,563,036 B2 | Page 1 of 1 |
| APPLICATION NO. | : 13/148175 | |
| DATED | : October 22, 2013 | |
| INVENTOR(S) | : Eeckman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 64 days.

Signed and Sealed this
Third Day of March, 2015

Michelle K. Lee
*Deputy Director of the United States Patent and Trademark Office*